United States Patent
Kerl et al.

(10) Patent No.: US 10,835,478 B2
(45) Date of Patent: Nov. 17, 2020

(54) LIGHTENING METHOD USING SPECIAL SILOXANE COMPOUNDS

(71) Applicant: Henkel AG & Co. KGaA, Duesseldorf (DE)

(72) Inventors: Sylvia Kerl, Hamburg (DE); Camille Grosjacques, Hamburg (DE); Katharina Krause, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 495 days.

(21) Appl. No.: 15/747,763

(22) PCT Filed: Jun. 3, 2016

(86) PCT No.: PCT/EP2016/062603
§ 371 (c)(1),
(2) Date: Jan. 26, 2018

(87) PCT Pub. No.: WO2017/016719
PCT Pub. Date: Feb. 2, 2017

(65) Prior Publication Data
US 2018/0221269 A1    Aug. 9, 2018

(30) Foreign Application Priority Data
Jul. 28, 2015 (DE) .................. 10 2015 214 277

(51) Int. Cl.
| | | |
|---|---|---|
| *A61Q 5/08* | (2006.01) | |
| *A61K 8/892* | (2006.01) | |
| *A61K 8/58* | (2006.01) | |
| *A61Q 5/10* | (2006.01) | |
| *A61K 8/22* | (2006.01) | |

(52) U.S. Cl.
CPC ............... *A61K 8/892* (2013.01); *A61K 8/22* (2013.01); *A61K 8/585* (2013.01); *A61Q 5/08* (2013.01); *A61Q 5/10* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 2003/0106167 A1 | 6/2003 | Rose et al. | |
| 2004/0133996 A1 | 7/2004 | Wolff et al. | |
| 2006/0078517 A9* | 4/2006 | Gourlaouen | A61Q 5/08 424/63 |
| 2012/0308498 A1* | 12/2012 | Hercouet | A61Q 5/10 424/62 |
| 2014/0004073 A1 | 1/2014 | Yu | |

FOREIGN PATENT DOCUMENTS

| | | |
|---|---|---|
| WO | 2011076603 A2 | 6/2011 |
| WO | 2015086268 A1 | 6/2015 |

OTHER PUBLICATIONS

EPO, International Search Report and Written Opinion issued in International Application No. PCT/EP2016/062603, dated Jul. 11, 2016.
"Some challenges in modern hair colour formulations" International Journal of Cosmetic Science 21; presented on Apr. 22, 1998 at SCS Spring Conference in London, UK.

* cited by examiner

*Primary Examiner* — Jyothsna A Venkat
(74) *Attorney, Agent, or Firm* — Lorenz & Kopf, LLP

(57) ABSTRACT

The present disclosure relates a method for the lightening of keratinous fibers, particularly human hair, wherein a lightening agent (AM) containing at least one special dimethylcyclosiloxane and at least one special polydimethylsiloxane is used. Use of the special siloxanes results in improved care of the keratinous fibers with simultaneous improvement of the lightening effect. Furthermore, the present disclosure relates to a corresponding packaging unit (kit-of-parts) and the use of a combination of special siloxanes to improve the care of keratinous fibers while simultaneously improving the lightening effect.

2 Claims, No Drawings

LIGHTENING METHOD USING SPECIAL SILOXANE COMPOUNDS

CROSS-REFERENCE TO RELATED APPLICATION

This application is a U.S. National-Stage entry under 35 U.S.C. § 371 based on International Application No. PCT/EP2016/062603, filed Jun. 3, 2016 which was published under PCT Article 21(2) and which claims priority to German Application No. 10 2015 214 277.9, filed Jul. 28, 2015, which are all hereby incorporated in their entirety by reference.

TECHNICAL FIELD

The present disclosure relates a method for the lightening of keratinous fibers, wherein a lightening agent (AM) containing at least one special dimethylcyclosiloxane and at least one special polydimethylsiloxane is used. The use of these special siloxanes achieves improved care with simultaneously improved lightening effect.

BACKGROUND

Furthermore, the present disclosure relates to a packaging unit (kit-of-parts) including a cosmetic agent (M1) and an oxidant preparation (M2), wherein the cosmetic agent (M1) and/or the oxidant preparation (M2) contain at least one special dimethylcyclosiloxane and at least one special polydimethylsiloxane.

Finally, the present disclosure relates to the use of a combination of at least one special dimethylcyclosiloxane and at least one special polydimethylsiloxane to improve the care of keratinous fibers with simultaneous improvement of the lightening effect.

Changing the style and color of the hair constitutes an important area of modern cosmetics. The hair's appearance can be adapted both to current fashion trends and also to the particular preferences of each and every consumer. Coloring hair in a stylish manner or laminating graying or white hair with modern or natural color shades is normally achieved with use of color-changing agents. In addition to a strong color effect, this coloring method achieves additional features, such as increasing the hair volume.

According to the state of the art, various coloring methods for coloring the skin and/or keratinous fibers with which different color-changing cosmetic agents are used are known.

In coloring methods which achieve permanent, intensive coloring, so-called oxidative dyes are used. Said dyes usually contain oxidative dye precursors, so-called developer components and coupler components. The developer components join together or couple with one or more coupler components to form, under the influence of oxidants or atmospheric oxygen, the actual colorants per se. Indeed, the oxidative dyes are exemplified by outstanding, long-lasting color results. To achieve natural-looking colors, however, a mix from a large number of oxidative dye intermediates must normally be used; in many cases, partially-oxidizing dyes are still used to create the tinting effect.

In coloring methods resulting in temporary coloring, dyes or tints containing so-called partially-oxidizing agents are normally used as the coloring component. These are dye molecules that coat the substrate itself and do not require an oxidative process to create the color. These dyes include Henna, which has been known to color skin and hair since ancient times. Said dyes are usually much more sensitive to shampooing than oxidative dyes, and therefore a highly undesirable shade shift or a visible homogeneous color loss occurs at a much earlier time.

An alternative coloring method has finally aroused great interest. With this method, precursors of the natural hair dye melanin are applied to the substrate, e.g. hair; these then form, as part of the oxidative processes in the hair, natural-looking dyes. In said method, 5,6-dihydroxyindoline is used as the dye precursor. Particularly if agents containing 5,6-dihydroxyindoline are repeatedly applied, the natural hair color of people with graying hair can be restored. The color effect can be achieved by employing atmospheric oxygen as the only oxidant, thereby eliminating the need for further oxidants. In the case of people whose hair was originally medium-blond to brown, 5,6-dihydroxyindoline can be used as the only precursor. For application on people whose hair was originally red and more particularly dark to black, on the other hand, satisfactory results can often be achieved only if other dye components, more particularly special oxidative dye precursors, are also used.

However the coloring methods known in the state of the art, particularly lightening methods, do not always achieve the desired high coloring effect or have additional desired properties, such as improved care of the skin during or after the hair coloring.

The present disclosure therefore addressed the problem of preparing a method for lightening keratinous fibers which avoids, or at least diminishes, the disadvantages brought by the prior art and improves care of the skin with a simultaneously improved lightening effect.

Surprisingly, it was found that the use of at least one special dimethylcyclosiloxane and at least one polydimethylsiloxane in a lightening method achieves improved care, particularly for improved compatibility of the keratinous fibers with a simultaneously improved lightening effect.

BRIEF SUMMARY

Methods, package units, and uses of cosmetic agents are described. In one embodiment, a method for lightening keratinous fibers includes applying a lightening agent (AM) onto the keratinous fibers, wherein the lightening agent is produced immediately before application by combining at least one cosmetic agent (M1) and at least one oxidant preparation (M2). The lightening agent (AM) is left on the keratinous fibers for from about 10 to about 60 minutes at room temperature and/or at least about 45° C. The keratin fibers are then rinsed with water and/or a cleansing composition for from about 1 to about 5 minutes. The cosmetic agent (M1) and/or the oxidant preparation (M2) include at least one dimethylcyclosiloxane and at least one polydimethylsiloxane.

A package unit is provided in another embodiment. The package unit includes at least one container (C1) with a cosmetic agent (M1) and at least one container (C2) with an oxidant preparation (M2). The cosmetic agent (M1) and/or the oxidant preparation (M2) include at least one dimethylcyclosiloxane and at least one polydimethylsiloxane.

A use of a cosmetic agent is provided in yet another embodiment. The cosmetic agent is used to improve the care of keratinous fibers while simultaneously improving the lightening effect. The cosmetic agent includes a combination of at least one dimethylcyclosiloxane and at least one polydimethylsiloxane.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first subject of the present disclosure, therefore, is a method for lightening keratinous fibers, wherein the method comprises the following method steps in the specified sequence:
a) Application of a lightening agent (AM), which is produced immediately before application of at least one cosmetic agent (M1) and at least one oxidant preparation (M2), on the keratinous fibers,
b) leaving the lightening agent (AM) produced under step a) on the keratinous fibers for a duration of from about 10 to about 60 minutes, preferably from about 20 to about 45 minutes, at room temperature and/or at least about 45° C.,
c) rinsing the keratin fibers with water and/or a cleansing composition for from about 1 to about 5 minutes,
wherein the cosmetic agent (M1) and/or the oxidant preparation (M2) in a cosmetically compatible carrier contains
(i) at least one dimethylcyclosiloxane of the formula (I)

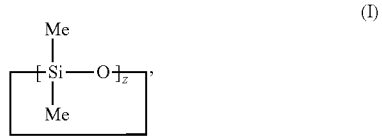

wherein
z denotes integers from 3 to about 12, and
(ii) at least one polydimethylsiloxane of the formula (II)

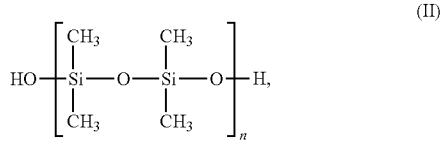

wherein n denotes integers from about 1,800 to about 28,000.

As contemplated herein, the expressions "keratinous fibers and keratin fibers" suggest fur, wool, feathers as well as human hair. According to the present disclosure, it is particularly preferable if the method is used for lightening human hair.

Furthermore, in the context of the present disclosure, the term "method for lightening" is understood to mean use of said method results in a lighter coloring of keratinous fibers than before the lightening method. The lightening methods of the present disclosure can be used for lightening of natural color and for lightening of already dyed keratinous fibers.

In addition, "room temperature" according to the present disclosure means the ambient temperature that prevails without the effect of external heat and amounts to preferably from about 10 to about 39° C.

Furthermore, in the context of the present disclosure, the term "cleaning composition" is understood to mean a composition which has a cleaning effect and therefore contains at least one surfactant. Surfactants according to the present disclosure are amphiphilic (bifunctional) compounds, which include at least one hydrophobic and at least one hydrophilic molecular part. A basic property of surfactants is the oriented absorption at boundary surfaces, as well as the aggregation to micelles and the formation of lyotropic phases.

Furthermore, the term "combability" in the context of the present disclosure is understood to mean the combability of wet fibers and the combability of dry fibers.

In addition, the term "fatty alcohols" according to the present disclosure means aliphatic, long-chained, monovalent, primary alcohols, which have unbranched hydrocarbon radicals containing from about 6 to about 30 carbon atoms. The hydrocarbon radicals can be either saturated or mono- or polyunsaturated.

Finally, the expression "fatty acids" according to the present disclosure means aliphatic monocarboxylic acids with unbranched carbon radicals, which have hydrocarbon radicals containing from about 6 to about 30 carbon atoms. The hydrocarbon radicals can be either saturated or mono- or polyunsaturated.

Unless otherwise specified, the total quantity with respect to the components of the cosmetic agent (M1) and/or oxidant preparation (M2) as contemplated herein refers to the total quantity of active substance for the respective component.

In method step a) of the present disclosure, the production of a lightening agent (AM) is achieved by mixing a cosmetic agent (M1) with an oxidant preparation (M2). In the context of the present disclosure, it has been found to be advantageous if the cosmetic agent (M1) is mixed with the oxidant preparation (M2) in specific ratios. Preferred methods as contemplated herein are exemplified in that, in method step a), the cosmetic agent (M1) is mixed with the oxidant preparation (M2) in the weight ratio from about 3:1 to about 1:3, preferably from about 2:1 to about 1:2, particularly 1:2. Application of the lightening agent (AM) produced by mixing normally takes place by hand by the user. Personal protective clothing is preferably worn in the process, more particularly protective gloves, preferably from plastic or latest for one-time use (disposable gloves), as well as an apron. However, the lightening agent (AM) can also be applied to the keratinous fibers by employing an application aid.

In method step b), lightening agent (AM) produced in step a) is left on the keratinous fibers at room temperature and/or at least about 45° C. In the process, it is possible to leave the lightening agent (AM) on the hair at room temperature and then increase the temperature to at least about 45° C. By increasing the temperature, i.e. with the addition of heat externally by a heating hood, the lightening effect of the method can be enhanced.

After the dwell time in method b) has ended, the remaining lightening agent (AM) is washed off of the keratinous fibers using a cleaning preparation, which preferably contains at least one cationic and/or anionic and/or nonionic surfactant and/or water (method c). This method step c) is optionally repeated an additional time.

In the context of the present disclosure, it can also be advantages to apply a post-treatment agent on the keratinous fibers after method step c) in a subsequent method step d). This post-treatment agent can, for example, be a conditioning agent which contains at least one conditioning compound from the group of cationic polymers, silicone derivatives and oils. Therefore, in the context of the present disclosure, it is preferable if a post-treatment agent is applied to the keratinous fibers after method step c) in a method step d) and is then rinsed off after a period of from about 1 to about 10 minutes.

As contemplated herein, it is preferable that method steps a) to d) are carried out in the sequence specified above with an interval of from about 0 to about 60 minutes, preferably from about 0 to about 40 minutes, particularly from about 0 to about 30 minutes between the individual method steps.

The lightening agent (AM) used in the method contains at least one special dimethylcyclosiloxane of formula (I).

As contemplated herein, it has been found to be advantageous if dimethylcyclosiloxanes with a specific ring size are used. As contemplated herein, preference is given to methods exemplified in that z in formula (I) denotes integers from 3 to about 10, preferably from 4 to about 8, more preferably from 4 to about 6, particularly 5.

Particularly good results with regard to the lightening effect and the care effect are achieved if dimethylcyclosiloxane of formula (Ia) is used. Therefore, in the context of the present disclosure, it is particularly preferred that the at least one dimethylcyclosiloxane (i) in the cosmetic agent (M1) and/or in the oxidant preparation (M2) has formula (Ia)

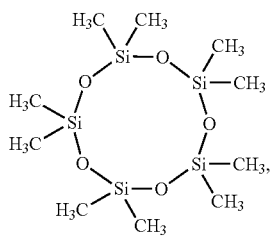

Preference is given to use of the at least one dimethylcyclosiloxane (i) in a cosmetic agent (M1) and/or the oxidant preparation in specific quantity ranges. As contemplated herein, advantageous methods are thus exemplified in that the cosmetic agent (M1) and/or the oxidant preparation (M2) contains the at least one dimethylcyclosiloxane (i) of formula (I) and/or formula (Ia) in a total amount of from about 0.1 to about 17 wt. %, preferably from about 0.5 to about 8.5 wt. %, preferably from about 1.0 to about 6.0 wt. %, particularly from about 1.2 to about 4.5 wt. % relative to the total weight of the cosmetic agent (M1) and/or the oxidant preparation (M2). Use of the at least one dimethylcyclosiloxane of formula (I) and/or formula (Ia) in the aforementioned quantity ranges achieves a particularly high care- and/or lightening effect of the method.

Furthermore, the lightening agent (AM) used in the method contains at least one polydimethylsiloxane of formula (II).

In the scope of the present disclosure, use of polydimethylsiloxane (ii) with a specific molecular weight is advantageous. Preferred embodiments of the present disclosure are therefore exemplified in that the at least one polydimethylsiloxane (ii) of formula (II) in the cosmetic agent (M1) and/or the oxidant preparation (M2) has an average molecular weight $M_w$ of from about 140,000 to about 2,000,000 Da, preferably from about 150,000 to about 1,900,000 Da, more preferably from about 160,000 to about 1,800,000 Da, particularly from about 170,000 to about 1,700,000 Da. The average molecular weight $M_w$ can, for example, be determined by employing gel permeation chromatography (GPC) Liu X. M. et. al.; "Comparative Studies of Poly(Dimethyl-Siloxanes) Using Automated GPC-MALDI-TOF MS and On-Line GPC-ESI-TOF MS"; Am. Soc. Mass. Spectrom., 2003, 14, pages 195 to 202).

Furthermore, with regard to the improved care- and/or lightening effect of the method, it has been found to be advantageous if the polydimethylsiloxane (ii) of formula (II) has a specific viscosity. Preferred methods are therefore exemplified in that the at least one polydimethylsiloxane (ii) of formula (II) in cosmetic agent (M1) and/or the oxidant preparation (M2) has a viscosity at 25° C. of from about 100,000 to about 100,000,000 mPa*s, preferably from about 200,000 to about 100,000,000 mPa*s, more preferably from about 300,000 to about 100,000,000 mPa*s, particularly from about 400,000 to about 100,000,000 mPa*s. The viscosity of the polydimethylsiloxane (ii) can, for example, be determined as describe in the application document US 2014/0004073 A1.

As contemplated herein, the at least one polydimethylsiloxane (ii) is preferably used in specific quantity ranges. Therefore, as contemplated herein, it is preferable that the cosmetic agent (M1) and/or the oxidant preparation (M2) contains the at least one polydimethylsiloxane (ii) of formula (II) in a total amount of from about 0.005 to about 3.0 wt. %, preferably from about 0.05 to about 1.5 wt. %, preferably from about 0.1 to about 1.2 wt. %, particularly from about 0.2 to about 1.0 wt. % relative to the total weight of the cosmetic agent (M1) and/or the oxidant preparation (M2). Use of the at least one polydimethylsiloxane (ii) of formula (II) in the aforementioned quantity ranges with the at least one dimethylcyclosiloxane of formula (I) and/or formula (Ia) achieves an especially high care- and/or lightening effect of the method.

Particularly good results with regard to the care- and/or lightening effect are also achieved if the cosmetic agent (M1) and/or the oxidant preparation (M2) contains the at least one dimethylcyclosiloxane (i) of formula (I) and/or formula (Ia) and the at least one polydimethylsiloxane (ii) in specific weight ratios. Preferred methods as contemplated herein are therefore exemplified in that the weight ratio of the at least one dimethylcyclosiloxane (i) of formula (I) and/or formula (Ia) to the at least one polydimethylsiloxane (ii) of formula (II) in the cosmetic agent (M1) and/or the oxidant preparation (M2) is from about 20:1 to about 1:1, preferably from about 15:1 to about 2:1, preferably from about 10:1 to about 3:1, particularly from about 6:1 to about 4:1. The weight ratio specified above relates to the respective total amounts of the at least one dimethylcyclosiloxane (i) of formula (I) and/or formula (Ia) and at least one polydimethylsiloxane (ii) of formula (II).

In particularly preferred methods of the present disclosure, the cosmetic agent (M1) and/or the oxidant preparation (M2) contains a dimethylcyclosiloxane of formula (Ia) and a special polydimethylsiloxane (ii) of formula (II). Therefore, as contemplated herein, it is preferred that the cosmetic agent (M1) and/or the oxidant preparation (M2)
(i) contains at least one dimethylcyclosiloxane of the formula (Ia)

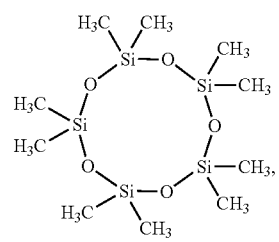

and
(ii) at least one polydimethylsiloxane of the formula (II)

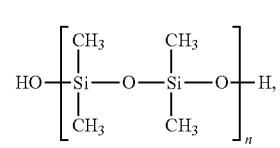

wherein
n denotes from about 1,800 to about 28,000.

With regard to the care- and lightening effect, it has been found to be particularly advantageous if a dimethylcyclosiloxane of formula (Ia) and a special polydimethylsiloxane of formula (II) are contained in the cosmetic agent (M1) and/or oxidant preparation (M2) in specific amounts and weight ratios. Particularly preferred methods are therefore exemplified in that the cosmetic agent (M1) and/or the oxidant preparation (M2) contains—relative to the total weight of cosmetic agent (M1) and/or oxidant preparation (M2)—
(i) at least one dimethylcyclosiloxane of the formula (Ia) in a total amount of from about 1.2 to about 4.5 wt. %

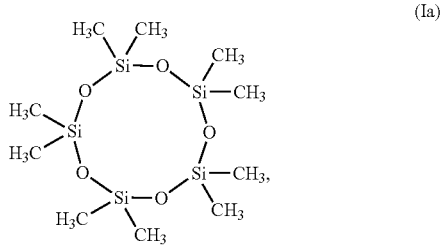

(ii) at least one polydimethylsiloxane of the formula (II) in a total amount of from about 0.2 to about 1.0 wt. %

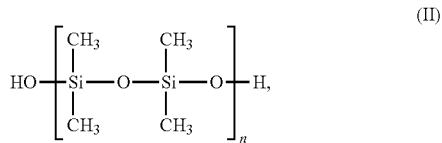

wherein
n denotes from about 1,800 to about 28,000,
wherein the weight ratio of the at least one dimethylcyclosiloxane (i) of formula (Ia) to the at least one polydimethylsiloxane (ii) of formula (II) in the cosmetic agent (M1) and/or the oxidant preparation (M2) is from about 6:1 to about 4:1. Use of the aforementioned siloxanes in the cosmetic agent (M1) and/or oxidant preparation (M2) achieves an improved care- and/or lightening effect in comparison with lightening methods in which the aforementioned combination is not used.

The cosmetic agents (M1) and the oxidant preparation (M2l) used in the method contain the aforementioned siloxanes of formulae (I) and/or (Ia) and (II) in a cosmetic carrier. As contemplated herein, the cosmetically compatible carrier is hydrous, alcoholic or hydrous-alcoholic. According to the present disclosure, creams, emulsions, gels or surfactant-containing, foaming solutions for example, such as shampoos, foam aerosols or other preparations suitable for application on the hair, can be used.

As contemplated herein, a hydrous carrier contains at least about 30 wt. %, more particularly at least about 50 wt. %, of water relative to the total weight of the cosmetic agent (M1) or oxidant preparation (M2).

According to the present disclosure, hydrous-alcoholic carriers mean aqueous compositions, containing a $C_1$-$C_4$ alcohol in a total quantity of from about 3 to about 90 wt. %, relative to the total weight of the cosmetic agent (M1) or oxidant preparation (M2), more particularly ethanol and/or isopropanol.

The cosmetic agent (M1) and the oxidant preparation (M2) used as contemplated herein can additionally contain other organic solvents, such as methoxybutanol, ethyldiglycol, 1,2-propylenglycol, n-propanol, n-butanol, n-butyleneglycol, glycerin, diethyleneglycolmonoethylether, and Diethyleneglycolmono-n-butylether. All water-soluble organic solvents are preferred, wherein the solvent is contained in a total quantity of from about 0.1 to about 30 wt. %, preferably from about 1 to about 20 wt. %, more particularly from about 2 to about 10 wt. %, relative to the total weight of the cosmetic agent (M1) or the oxidant preparation (M2).

The cosmetic agent (M1) used as contemplated herein can also contain a dyeing, particularly a lightening compound. In the context of the present disclosure, preference is given to a cosmetic agent (M1) which also contains at least one dyeing compound, selected from the group of oxidative dye intermediates, partially-oxidizing dyes and mixtures thereof.

In a preferred embodiment, the cosmetic agent (M1) contains at least one oxidative dye precursor.

On the basis of their reaction behavior, oxidative dye precursors can be divided into two categories, so-called developer components and coupler components. Developer components can combine together to form the actual dye. They can also contain cosmetic agents (M1) used as contemplated herein as the sole compounds. Therefore, in a preferred embodiment, the cosmetic agents (M1) contain at least one oxidation dye precursor of the developer type. Within the scope of the present disclosure, however, it may be that the cosmetic agent (M1) contains at least one oxidative dye precursor of the coupler type. Particularly good results with respect to the coloration of keratin fibers are achieved when the cosmetic agent (M1) contain at least one oxidative dye precursor of the developer type and at least one oxidative dye precursor product of the coupler type.

The developer and coupler components are normally used in a free form. In the case of substances with amino groups, however, use of the salt form thereof, more particularly in the form of hydrochlorides and hydrobromides or sulfates, may be preferred.

As contemplated herein, the preference is for cosmetic agents (M1) which contain the developer and/or coupler components, each in a total quantity of from about 0.001 to about 10 wt. %, preferably from about 0.01 to about 8 wt. %, more preferably from about 0.1 to about 5 wt. %, most preferably from about 0.5 to about 3 wt. %, relative to the total weight of the cosmetic agent.

In another preferred embodiment, the cosmetic agent (M1) used as contemplated herein contains an oxidative dye precursor of the developer and/or coupler components in a total quantity of from about 0.001 to about 10 wt. %, preferably from about 0.01 to about 8 wt. %, more preferably from about 0.1 to about 5 wt. %, most preferably from about 0.5 to about 3 wt. %, relative to the total weight of the cosmetic agent.

Suitable oxidative dye precursors of the developer type are typically p-phenylenediamine and the derivatives thereof. Preferred p-phenylenediamines are selected from one or multiple compounds of the group, which is formed from p-phenylenediamine, p-toluenediamine, 2-chloro-p-phenylenediamine, 2,3-dimethyl-p-phenylenediamine, 2,6-dimethyl-p-phenylenediamine, N,N-bis-(2-hydroxyethyl)-p-phenylene-diamine, 2-(2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyloxy)-p- phenylenediamine and N-(4-amino-3-methyl-phenyl)-N-[3-(1H-imidazol-1-yl)propyl]amine, as well as the physiologically-tolerable salts thereof.

As contemplated herein, use of compounds containing at least two aromatic rings, which are substituted with amino and/or hydroxyl groups, as the developer components may be preferred. Preferred two-ring developer components are selected from N,N'-bis-(2-hydroxyethyl)-N,N'-bis-(4'-aminophenyl)-1,3-diaminopropan-2-ol, N,N'-bis-(4-aminophenyl)-1,4-diazacycloheptane, bis-(2-hydroxy-5-aminophenyl)methane, as well as the physiologically-tolerable salts thereof.

As contemplated herein, use of a p-aminophenol derivative or one of the physiologically-tolerable salts thereof as the developer component may also be preferred. Preferred p-aminophenols are p-aminophenol, N-methyl-p-aminophenol, 4-amino-3-methylphenol, 4-amino-2-aminomethylphenol, 4-amino-2-(1,2-dihydroxyethyl)phenol, 4-amino-2-(diethylaminomethyl)phenol, as well as the physiologically-tolerable salts thereof.

The developer components can also be selected from o-aminophenol and the derivatives thereof, preferably from 2-amino-4-methylphenol, 2-amino-5-methylphenol, 2-amino-4-chlorphenol and/or the physiologically-tolerable salts thereof.

Moreover, the developer components can be selected from heterocyclic developer components, such as pyrimidine derivatives, pyrazole derivatives, pyrazolopyrimidine derivatives and/or the physiologically-tolerable salts thereof. Preferred pyrimidine derivatives are 2,4,5,6-tetraaminopyrimidine, 4-hydroxy-2,5,6-triaminopyrimidine and the physiologically-tolerable salts thereof. A preferred pyrazole derivative is 4,5-diamino-1-(2-hydroxyethyl)pyrazole, as well as the physiologically-tolerable salts thereof. Pyrazolo[1,5-a]pyrimidine are particularly preferred as pyrazolopyrimidines.

Preferred oxidative dye precursors of the developer type are selected from the group formed from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxy-ethyl)-N,N'-bis-(4-aminophenyl)-1,3-diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecan, p-aminophenol, 4-amino-3-methylphenol, 4-amino-2-amino-methylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraamino-pyrimidine, 4-hydroxy-2,5,6-triaminopyrimidine, 2-hydroxy-4,5,6-triaminopyrimidine or the physiologically-tolerable salts thereof.

Particularly preferred developer components are p-toluenendiamine, 2-(2-hydroxyethyl)-p-phenylene-diamine, 2-methoxymethyl-p-phenylenediamine, N-(4-amino-3-methylphenyl)-N-[3-(1H-imidazol-1-yl)-propyl)amine, and/or 4,5-diamino-1-(2-hydroxyethyl)pyrazole, as well as the physiologically-tolerable salts thereof.

According to another preferred embodiment of the present disclosure, the cosmetic agent (M1) as contemplated herein contains, as oxidative dye precursors, at least one coupler component in addition to at least one developer component. m-phenylenediamine derivatives, naphthols, resorcin and resorcin derivatives, pyrazolones and m-aminophenol derivatives are typically used as coupler components.

Preferred coupler components as contemplated herein are selected from
(A) m-aminophenol and the derivatives thereof, more particularly 3-aminophenol, 5-amino-2-methylphenol, 3-amino-2-chloro-6-methylphenol, 5-amino-4-chloro-2-methylphenol, 5-(2'-hydroxyethyl)-amino-2-methylphenol and 2,4-dichloro-3-aminophenol,
(B) o-aminophenol and the derivatives thereof, such as 2-amino-5-ethylphenol,
(C) m-Diaminobenzene and the derivatives thereof, such as 2,4-diaminophenoxy-ethanol, 1,3-bis-(2',4'-diaminophenoxy)-propane, 1-methoxy-2-amino-4-(2'-hydroxyethylamino) benzene, 2,6-bis-(2'-hydroxyethylamino)-1-methylbenzenel, 2-({3-[(2-Hydroxyethyl)amino]-4-methoxy-5-methylphenyl}amino)ethanol and 2-({3-[(2-hydroxyethyl)amino]-2-methoxy-5-methylphenyl}-amino)ethanol,
(D) o-diaminobenzene and the derivatives thereof,
(E) di and/or trihydroxybenzene derivatives, more particularly resorcin, 2-chlororesorcin, 4-chlororesorcin, 2-methylresorcin and 1,2,4-trihydroxybenzene,
(F) pyridine derivatives, more particularly 3-amino-2-methylamino-6-methoxypyridine, 2,6-diamino pyridine, 2,6-dihydroxy-3,4-dimethylpyridine, 2-amino-3-hydroxy-pyridine and 3,5-diamino-2,6-dimethoxy-pyridine,
(G) naphthalene derivatives, such as 1-naphthol and 2-methyl-1-naphthol,
(H) morpholine derivatives, such as 6-hydroxybenzomorpholine,
(I) quinoxaline derivatives,
(J) pyrazole derivatives, such as 1-phenyl-3-methylpyrazol-5-on,
(K) indol derivatives, such as 6-hydroxyindol,
(L) pyrimidine derivatives or
(M) methylendioxybenzene derivatives, such as 1-(2'-Hydroxyethyl)-amino-3,4-methylenedioxybenzene
and their physiologically compatible salts.

Coupler components preferred as contemplated herein are selected from the group, which is formed from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl)amino)ethanol, 2-({3-[(2-hydroxyethyl)amino]-4,5-dimethylphenyl}amino)ethanol, 2-[3-morpholine-4-ylphenyl)amino]ethanol, 3-amino-4-(2-methoxy-ethoxy)-5-methylphenylamine, 1-amino-3-bis-(2-hydroxyethyl)aminobenzene, resorcin, 2-methylresorcin, 4-chlororesorcin, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-on, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or the physiologically-tolerable salts of the aforementioned compounds.

Preferred coupler components as contemplated herein are resorcin, 2-methylresorcin, 4-chlororesorcin, 5-amino-2- methylphenol, 3-aminophenol, 2-(2,4-diaminophenoxy) ethanol, 1,3-bis-(2,4-diamino-phenoxy)propane, 1-methoxy-2-amino-4-(2'-hydroxyethylamino)benzene, 2-amino-3-hydroxypyridine, 2,6-dihydroxy-3,4-dimethylpyridine, 1,5-dihydroxynaphthalene, 2,7-dihydroxynaphthalene and 1-naphthol, as well as the physiologically-tolerable salts thereof.

In a particularly preferred embodiment of the present disclosure, the cosmetic agents as contemplated herein are exemplified in that they contain at least one developer component, selected from the group of p-phenylenediamine, p-toluenediamine, N,N-bis-(2-hydroxyethyl)amino-p-phenylenediamine, 1,3-bis-[(2-hydroxyethyl-4'-aminophenyl)amino]-propan-2-ol, 1,10-bis-(2',5'-diaminophenyl)-1,4,7,10-tetraoxadecane 4-aminophenol, 4-amino-3-methylphenol, bis-(5-amino-2-hydroxyphenyl)methane, 2,4,5,6-tetraaminopyrimidine, 2-hydroxy-4,5,6-triaminopyrimidine, 4,5-diamino-1-(2-hydroxyethyl)-pyrazole, the physiologically-tolerable salts thereof and the mixtures thereof, and at least one coupler component, selected from the group of resorcin, 2-methylresorcin, 5-methylresorcin, 2,5-dimethylresorcin, 4-clororesorcin, resorcin monomethylether, 5-aminophenol, 5-amino-2-methylphenol, 5-(2-hydroxyethyl)amino-2-methylphenol, 3-amino-4-chloro-2-methylphenole, 3-amino-2-chloro-6-methylphenol, 3-amino-2,4-dichlorophenol, 2,4-diaminophenoxyethanol, 2-amino-4-(2-hydroxyethyl)amino-anisolsulfate, 1,3-bis-(2,4-diaminophenoxy)propane, 2-amino-3-hydroxypyridine, 2-methylamino-3-amino-6-methoxypyridine, 2,6-dihydroxy-3,4-dimethylpyridine, 3,5-diamino-2,6-dimethoxypyridine, 1-naphthol, 2-methyl-1-naphthol, 1,5-dihydroxynaphthalene, 2,7-dihydroxynaphthalene, 1-phenyl-3-methylpyrazol-5-on, 2,6-bis-[(2-hydroxyethyl)amino]-toluene, 4-hydroxyindol, 6-hydroxyindol, 6-hydroxybenzomorpholine, the physiologically-tolerable salts thereof and the mixtures thereof.

In order to obtain a balanced and subtle tint formation, the present disclosure may specify that the cosmetic agents (M1) additionally contain at least one partially-oxidizing dye. Partially-oxidizing dyes are dyes that coat the substrate itself and do not require an oxidative process to create the color. Partially-oxidizing dyes are usually nitro-phenylenediamines, nitroaminophenols, azo dyes, anthraquinones or indophenols.

Partially-oxidizing dyes can be sub-divided into anionic, cationic and non-ionic partially-oxidizing dyes.

Preferred anionic partially-oxidizing dyes are the compounds known under the designations Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenol blue. Preferred cationic partially-oxidizing dyes are cationic triphenylmethane dyes, such as Basic Blue 7, Basic Blue 26, Basic Violet 2 and Basic Violet 14, as well as aromatic systems, which are substituted with a quaternary nitrogen group, such as Basic Yellow 57, Basic Red 76, Basic Blue 99, Basic Brown 16 and Basic Brown 17 and HC Blue 16, as well as Basic Yellow 87, Basic Orange 31 and Basic Red 51. Preferred non-ionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-Ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

Moreover, partially-oxidizing dyes that occur in nature, such as Henna red, Henna neutral, Henna black, chamomile blossoms, sandalwood, black tea, walnut, Cascara bark, sage, logwood, madder root, catechu, ceder and alkanna root, can also be used.

As contemplated herein, the preference is for cosmetic agents (M1) which contain the partially-oxidizing agent in a total quantity of from about 0.001 to about 10 wt. %, preferably from about 0.01 to about 8 wt. %, more preferably from about 0.1 to about 5 wt. %, most preferably from about 0.5 to about 3 wt. %, relative to the total weight of the cosmetic agent.

The cosmetic agents (M1) as contemplated herein can contain other active ingredients and additives. According to the present disclosure, it is therefore preferable for the cosmetic agent (M1) to contain in addition at least one other compound, selected from the group of (i) thickening agents; (ii) linear or branched, saturated or unsaturated alcohols with from about 8 to about 20 carbon atoms; (iii) surfactants, particularly amphoteric surfactants; (iv) alkalizing agents; (v) oils; as well as (vi) the mixtures thereof.

Preferably, the cosmetic agents (M1) as contemplated herein are formulated as free-flowing preparations. The cosmetic agents (M1) must be formulated in such a manner that they are obtained after mixture with an oxidant preparation (M2) in lightening agents, which can be readily applied and distributed at the place of use on the one hand, but on the other are adequately viscous such that they remain at the site of action and do not run during the exposure time.

It has proven advantageous according to the present disclosure for the cosmetic agent (M1) as contemplated herein to contain at least one thickening agent from the group of (i) anionic, synthetic polymers; (ii) cationic, synthetic polymers; (iii) naturally occurring thickening agents, such as non-ionic guar gums, scleroglucan gums or xanthan gums, gum arabic, Ghatti gum, Karaya gum, gum tragacanth, Carrageen rubber, Agar-Agar, locust bean gum, pectines, alginates, starch fractions and derivatives, such as amylose, amylopectin and dextrins, as well as cellulose derivatives, such as methyl cellulose, carboxyalkyl celluloses and hydroxyalkyl celluloses; (iv) non-ionic synthetic polymers, such as polyvinyl alcohol or polyvinylpyrrolidone; (v) inorganic thickening agents, more particularly phyllosilicates, such as bentonite, more particularly smectites, such as montmorillonite or hectorite; as well as (vi) the mixtures thereof, in a total quantity of from about 0.0005 to about 5.0 wt. %, preferably from about 0.001 to about 3.0 wt. %, more preferably from about 0.005 to about 1.0 wt. %, most preferably from about 0.008 to about 0.01 wt. %, relative to the total weight of the cosmetic agent.

It has proven advantageous according to the present disclosure for the cosmetic agent as contemplated herein to contain, as the thickening agent, at least one naturally occurring thickening agent, more particularly Xanthan gum, as well as the salts thereof, of from about 0.0005 to about 5.0 wt. %, preferably from about 0.001 to about 1.0 wt. %, more preferably from about 0.005 to about 0.5 wt. %, most preferably from about 0.01 to about 0.1 wt. %, relative to the total weight of the cosmetic agent.

According to the present disclosure, it can be preferable for the linear or branched, saturated or unsaturated alcohol with 8 or 20 carbon atoms to be selected from the group of myristyl alcohol (1-tetradecanol), stearyl alcohol (1-octadecanol), cetearyl alcohol, 2-octyldodecanol, arachyl alcohol (eicosan-1-ol), gadoleyl alcohol ((9Z)-eicos-9-en-1-ol), arachidon alcohol ((5Z,8Z, 11Z, 14Z)-eicosa-5,8, 11,14-tetraen-1-ol), preferably 2-octyldodecanol and/or cetearyl alcohol, and in a total quantity of from about 1.0 to about 35 wt. %, preferably from about 5.0 to about 30 wt. %, more preferably from about 10 to about 25 wt. %, most preferably from about 12 to about 20 wt. %, relative to the total weight of the cosmetic agent.

Preferably, the cosmetic agents (M1) used as contemplated herein can also contain at least one partial ester from a polyol with from 2 to about 6 carbon atoms and linear saturated carbon atoms with from about 12 to about 30, more particularly from about 14 to about 22 carbon atoms, wherein the partial ester can be hydroxylated, in a total quantity of 0.5 to 10 wt. %, more particularly from about 3.0 to about 8.0 wt. %, relative to the total weight of the cosmetic agent. Said partial esters are more particularly the mono and diesters of glycerin or the monoesters of propyleneglycol or the mono and diesters of ethyleneglycol or the mono, di, tri and tetraesters of pentaerythritol, each with linear saturated $C_{12}$-$C_{30}$ carboxylic acids, which can be hydroxylated, more particularly those with palmitic and stearic acids, the sorbitan mono-, -di- or -triesters of linear saturated $C_{12}$-$C_{30}$ carboxylic acids, which can be hydroxylated, more particularly those of myristin acids, palmitic acids, stearic acids or of mixtures of said fatty acids and the methylglucose mono- and diesters of linear saturated $C_{12}$-$C_{30}$ carboxylic acids, which can be hydroxylated.

According to the present disclosure, the cosmetic agent (M1) as contemplated herein can contain at least one polyol partial ester, selected from glycerin monostearate, glycerin monopalmitate, glycerin distearate, glycerin dipalmitate, ethylene glycol monostearate, ethylene glycol mono palmitate, ethylene glycol distearate, ethylene glycol dipalmitate, as well as the mixtures thereof, more particularly mixtures from glycerin monostearate, glycerin monopalmitate, glycerin distearate and glycerin dipalmitate in a total quantity of from about 0.5 to about 10 wt. %, more particularly from about 3.0 to about 8.0 wt. %, relative to the total weight of the cosmetic agent.

The use of the aforementioned alcohols, partial esters and polypartial esters in the cosmetic agent (M1) used as contemplated herein can be particularly preferred if the cosmetic agent as contemplated herein exists in the form of an oil-in-water emulsion.

According to the present disclosure, the cosmetic agent (M1) as contemplated herein can also contain at least one surfactant. Surfactants according to the present disclosure are amphiphilic (bifunctional) compounds, which include at least one hydrophobic and at least one hydrophilic molecular part. A basic property of surfactants and emulsifiers is the oriented absorption at boundary surfaces, as well as the aggregation to micelles and the formation of lyotropic phases.

According to a preferred embodiment of the present disclosure, the cosmetic agents (M1) used as contemplated herein contain at least one amphoteric surfactant in a total quantity of from about 0.1 to about 5.0 wt. %, more particularly from about 0.2 to about 2.0 wt. %, relative to the total weight of the cosmetic agent. Amphoteric and/or zwitterionic surfactants are surface active compounds, which have at least one quaternary ammonium group and at least one —COO(—)— or —SO3(—)_group.

According to the present disclosure, the compounds below are particularly preferred amphoteric surfactants:
  alkylbetaines with from about 8 to about 20 carbon atoms in the alkyl group,
  amidopropylbetaines with from about 8 to about 20 carbon atoms in the acyl group,
  sulfobetaines with from about 8 to about 20 carbon atoms in the acyl group and
  amphoacetates or amphodiacetates with from about 8 to about 20 carbon atoms in the acyl group.

In a particularly preferred embodiment, the cosmetic agents (M1) used as contemplated herein contain as surfactant at least one amphoteric surfactant, selected from amidopropylbetaines with from about 9 to about 13 carbon atoms in the acyl group, in a total quantity of from about 0.1 to about 5.0 wt. %, more particularly from about 0.2 to about 2.0 wt. %, relative to the total weight of the cosmetic agent (M1).

The cosmetic agents (M1) used as contemplated herein can also contain at least one ethoxylated non-ionic surfactant in a total quantity of from about 0.5 to about 6.0 wt. %, more particularly from about 1.0 to about 4.0 wt. %, relative to the total weight of the cosmetic agent. It has proven particularly advantageous for the ethoxylated non-ionic surfactant to have a HLB value of above about 10, preferably above about 13. For this purpose, the nonionic surfactant must have a sufficiently high ethoxylization degree. In this context, therefore, the cosmetic agent (M1) contains at least one ethoxylated surfactant with at least about 12 ethylene oxide units as an ethoxylated surfactant. In addition to the correspondingly ethoxylated fatty alcohols, more particularly lauryl alcohol, myristyl alcohol, cetyl alcohol, stearyl alcohol, arachyl alcohol and behenyl alcohol, the present disclosure states that the sediments of 20 to 60 mol of ethylenoxide for castor oil and hydrogenated castor oil are particularly suitable. The at least one ethoxylated non-ionic surfactant is preferably selected from surfactants with the INGI designation ceteth-12, steareth-12, ceteareth-12, ceteth-20, steareth-20, ceteareth-20, ceteth-30, steareth-30, ceteareth-30, oleth-30, ceteareth-50, PEG-40 hydrogenated castor oil and PEG-60 hydrogenated castor oil, as well as mixtures of said substances, more preferably selected from ceteth-20, steareth-20, ceteareth-20, ceteth-30, steareth-30 and ceteareth-30.

Cosmetic agents (M1) according to the present disclosure usually have an alkaline pH value, more particularly between pH 8.0 and pH 12. These pH values are required to guarantee an opening of the external cuticle layer (cuticle) and facilitate a penetration of oxidative dye precursors and/or of the oxidant into the hair.

The aforementioned pH value can preferably be set using an alkalizing agent. According to the present disclosure, the alkalizing agent is selected from the group of (i) inorganic alkalizing agents; (ii) organic alkalizing agents; as well as (iii) the mixtures thereof, and in a total quantity of from about 1.5 to about 9.5 wt. %, preferably from about 2.5 to about 8.5 wt. %, more preferably from about 3.0 to about 8.0 wt. %, most preferably from about 3.5 to about 7.5 wt. %, relative to the total weight of the cosmetic agent (M1).

Preferred inorganic alkalizing agents are selected from the group formed from ammonia and/or ammonium hydroxide, i.e. hydrous solutions of ammonia, sodium hydroxide, potassium hydroxide, calcium hydroxide, barium hydroxide, sodium phosphate, potassium phosphate, sodium silicate, potassium silicate, sodium carbonate and potassium carbonate, as well as mixtures thereof. Ammonia and/or ammonium hydroxide is a most preferred alkalizing agent. Ammonia is most preferable in a total quantity of from about 0.1 to about 20 wt. %, preferably from about 0.5 to about 10 wt. %, more particularly from 1.0 to 7.0 wt. %, relative to the total weight of the cosmetic agent (M1).

Preferred organic alkalizing agents are selected from at least one alkanolamine. Alkanolamines preferred as contemplated herein are selected from alkanolamines from primary, secondary or tertiary amines with a $C_2$-$C_6$-alkyl base body, which carries at least one hydroxyl group. Particularly preferred alkanolamines are selected from the group formed from 2-aminoethan-1-ol (monoethanolamine), 3-aminopropan-1-ol, 4-amino-butan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methyl-propanol, 2-amino-2-methylbutanol, 3-amino-2-methylpropan-1-ol, 1-amino-2-methylpropan-2-ol, 3-aminopropan-1,2-diol, 2-amino-2-methylpropan-3-diol, 2-amino-2-ethyl-1,3-propanediol, N,N-dimethyl-ethanolamine, triethanolamine, diethanolamine and triisopropanolamine. Most preferred alkanolamines as contemplated herein are selected from the group of 2-aminoethan-1-ol (monoethanolamine), 2-amino-2-methylpropan-1-ol, 2-amino-2-methyl-propan-1,3-diol and triethanolamine. Particularly preferred cosmetic agents (M1) as contemplated herein contain a mixture of Monoethanolamine and 2-amino-2-methylpropan-1ol. It is preferable for the at least one alkanolamine to be contained in a total quantity of from about 0.05 to about 15 wt. %, more preferably from about 0.5 to about 10 wt. %, most preferably from about 3.5 to about 7.5 wt. %, relative to the total weight of the cosmetic agent.

Additional organic alkalization agents preferred as contemplated herein are selected from the group comprising L-arginine, D-arginine, D/L-arginine, L-lysine, D-lysine, D/L-lysine, as well as the mixtures thereof. Most preferred alkaline amino acids as contemplated herein are selected from L-arginine, D-arginine and D/L-arginine. Preferred cosmetic agents (M1) as contemplated herein contain at least one alkalizing agent that differs from alkanolamines and ammonia in a total quantity of from about 0.05 to about 5.0 wt. %, more particularly from about 0.5 to about 3.0 wt. %, relative to the total weight of the cosmetic agent (M1).

According to the present disclosure, the alkalizing agent is selected from the group of sodium hydroxide, potassium hydroxide, ammonia, monoethanolamine and 2-amino-2-methylpropane, particularly monoethanolamine and in a total quantity of from about 1.5 to about 9.5 wt. %, preferably from about 2.5 to about 8.5 wt. %, more preferably from about 3.0 to about 8.0 wt. %, most preferably from about 3.5 to about 7.5 wt. %, relative to the total weight of the cosmetic agent (M1).

In a particularly preferred embodiment, the cosmetic agents (M1) as contemplated herein contain a mixture of at least two different alkalizing agents, more particularly monoethanolamine and 2-amino-2-methylpropan-1-ol, in a total quantity of from about 0.05 to about 15 wt. %, preferably from about 0.5 to about 10 wt. %, preferably from about 3.5 to about 7.5 wt. %, relative to the total weight of the cosmetic agent (M1).

Preferably, the pH value of the cosmetic agent (M1) as contemplated herein, measured at about 22° C., is from about 8 to about 13, preferably from about 9.5 to about 12, more preferably from about 10 to about 11.5, most preferably from about 10.5 to about 11.

According to the present disclosure, it can also be preferable for the cosmetic agent (M1) to contain at least one oil, selected from the group of sunflower oil, corn oil, soya oil, pumpkin seed oil, grape seed oil, sesame oil, hazelnut oil, apricot seed oil, macadamia nut oil, arara oil, castor oil, avocado oil, as well as the mixtures thereof, in a total quantity of from about 0.1 to about 10 wt. %, preferably from about 0.2 to about 5.0 wt. %, more particularly from about 0.5 to about 2.0 wt. %, relative to the total weight of the cosmetic agent. The use of at least one of the aforementioned oils can significantly increase the nourishing effect of the combination of special siloxanes.

The cosmetic agent (M1) as contemplated herein most preferably contains grape seed oil in a total quantity of from about 0.1 to about 10 wt. %, preferably from about 0.2 to about 5.0 wt. %, more preferably from about 0.5 to about 2.0 wt. %, relative to the total weight of the cosmetic agent (M1).

The table below shows most preferred embodiments AF 1 to AF 28 of the cosmetic agent (M1) as contemplated herein (all values in wt. %, unless otherwise stated):

|  | AF 1 | AF 2 | AF 3 | AF4 |
|---|---|---|---|---|
| Dimethylcyclosiloxane of formula (I) | 0.1-17 | 0.5-8.5 | 1.0-6.0 | 1.2-4.5 |
| Polydimethylsiloxane of formula (II) | 0.005-3.0 | 0.05-1.5 | 0.1-1.2 | 0.2-1.0 |
| Cosmetic carrier [1] | Ad 100 | Ad 100 | Ad 100 | Ad 100 |
|  | AF 5 | AF 6 | AF 7 | AF 8 |
| Dimethylcyclosiloxane of formula (I) [2] | 0.1-17 | 0.5-8.5 | 1.0-6.0 | 1.2-4.5 |
| Polydimethylsiloxane of formula (II) [2] | 0.005-3.0 | 0.05-1.5 | 0.1-1.2 | 0.2-1.0 |
| Cosmetic carrier [1] | Ad 100 | Ad 100 | Ad 100 | Ad 100 |
|  | AF 9 | AF 10 | AF 11 | AF 12 |
| Dimethylcyclosiloxane of formula (Ia) | 0.1-17 | 0.5-8.5 | 1.0-6.0 | 1.2-4.5 |
| Polydimethylsiloxane of formula (II) [3] | 0.005-3.0 | 0.05-1.5 | 0.1-1.2 | 0.2-1.0 |
| Cosmetic carrier [1] | Ad 100 | Ad 100 | Ad 100 | Ad 100 |
|  | AF 13 | AF 14 | AF 15 | AF 16 |
| Dimethylcyclosiloxane of formula (Ia) [4] | 0.1-17 | 0.5-8.5 | 1.0-6.0 | 1.2-4.5 |
| Polydimethylsiloxane of formula (II) [4] | 0.005-3.0 | 0.05-1.5 | 0.1-1.2 | 0.2-1.0 |
| Cosmetic carrier [1] | Ad 100 | Ad 100 | Ad 100 | Ad 100 |

|  | AF 17 | AF 18 | AF 19 | AF 20 |
|---|---|---|---|---|
| Dimethylcyclosiloxane of formula (Ia) [4)] | 0.1-17 | 0.5-8.5 | 1.0-6.0 | 1.2-4.5 |
| Polydimethylsiloxane of formula (II) [4)] | 0.005-3.0 | 0.05-1.5 | 0.1-1.2 | 0.2-1.0 |
| Dyeing compound [5)] | 0.001-10 | 0.01-8 | 0.1-5 | 0.5-3 |
| Cosmetic carrier [1)] | Ad 100 | Ad 100 | Ad 100 | Ad 100 |

|  | AF 21 | AF 22 | AF 23 | AF 24 |
|---|---|---|---|---|
| Dimethylcyclosiloxane of formula (Ia) [4)] | 0.1-17 | 0.5-8.5 | 1.0-6.0 | 1.2-4.5 |
| Polydimethylsiloxane of formula (II) [4)] | 0.005-3.0 | 0.05-1.5 | 0.1-1.2 | 0.2-1.0 |
| Dyeing compound [5)] | 0.001-10 | 0.01-8 | 0.1-5 | 0.5-3 |
| Alkalizing agent [6)] | 0.0005-5.0 | 0.001-3.0 | 0.005-1.0 | 0.01-0.1 |
| Cosmetic carrier [1)] | Ad 100 | Ad 100 | Ad 100 | Ad 100 |

|  | AF 25 | AF 26 | AF 27 | AF 28 |
|---|---|---|---|---|
| Dimethylcyclosiloxane of formula (Ia) [4)] | 0.1-17 | 0.5-8.5 | 1.0-6.0 | 1.2-4.5 |
| Polydimethylsiloxane of formula (II) [4)] | 0.005-3.0 | 0.05-1.5 | 0.1-1.2 | 0.2-1.0 |
| Dyeing compound [5)] | 0.001-10 | 0.01-8 | 0.1-5 | 0.5-3 |
| Alkalizing agent [6)] | 0.0005-5.0 | 0.001-3.0 | 0.005-1.0 | 0.01-0.1 |
| Thickening agent [7)] | 0.0005-5.0 | 0.001-3.0 | 0.005-1.0 | 0.01-0.1 |
| Linear $C_8$-$C_{20}$ alcohol [8)] | 5.0 to 25 | 8.0 to 20 | 10 to 18 | 12 to 16 |
| Cosmetic carrier [1)] | Ad 100 | Ad 100 | Ad 100 | Ad 100 |

[1)] hydrous cosmetic carrier
[2)] weight ratio of dimethylcyclosiloxane of formula (I) to polydimethylsiloxane of formula (II) is from about 6:1 to about 4:1,
[3)] in formula (II), n denotes from about 1,800 to about 28,000,
[4)] weight ratio of dimethylcyclosiloxane of formula (I) to polydimethylsiloxane of formula (II) is from about 6:1 to about 4:1, in formula (II) n denotes from about 1,800 to about 28,000,
[5)] dyeing compound selected from oxidative dye intermediates of the developer type, oxidative dye intermediates of the coupler type, partially-oxidizing dyeing agents and mixtures thereof,
[6)] mixture of monoethanolamine and 2-Amino-2-methylpropan-1-ol
[7)] thickening agent selected from xanthan gum and salts thereof, particularly sodium salt,
[8)] linear $C_8$-$C_{20}$ alcohol is selected from 2-octyldodecanol, cetearylalcohol and mixtures thereof The oxidant preparation (M2) used as contemplated herein preferably contains at least one oxidant. The oxidants according to the present disclosure are different to atmospheric oxygen. Hydrogen peroxide, as well as the solid sediments for organic and inorganic compounds thereof, can be used as oxidants. As contemplated herein, the sediments for urea, melamine, polyvinylpyrrolidone, as well as sodium borate, can be used as solid sediments. Hydrogen peroxide and/or one of the solid sediments for organic or inorganic compounds thereof are the most preferred oxidants. As contemplated herein, the oxidant preparation (M2) contains at least one oxidant from the group of hydrogen peroxide and the addition products thereof on urea, melamine and sodium borate, particularly hydrogen peroxide, in a total amount of from about 0.5 to about 25 wt. %, preferably from about 4.0 to about 20 wt. %, more preferably from about 8.0 to about 13 wt. %, particularly from about 9.0 to about 12 wt. % relative to the total amount of oxidant preparation (M2). The total amount specified above relates to 100% hydrogen peroxide and/or 100% addition products of hydrogen peroxide.

A particularly preferable embodiment of the present disclosure is therefore exemplified in that, as an oxidant, hydrogen peroxide is contained in a total quantity of from about 0.5 to about 25 wt. %, preferably from about 4.0 to about 20 wt. %, more preferably from about 6.0 to about 15 wt. %, even more preferably from about 8.0 to about 13 wt. %, particularly from about 9.0 to about 12 wt. %, relative to the total weight of the oxidant preparation (M2). The calculation of the total quantity refers to 100% $H_2O_2$.

The oxidant preparations (M2) can also contain water in a total quantity of from about 40 to about 98 wt. %, more particularly from about 65 to about 85 wt. %, relative to the total weight of the oxidant preparation (M2).

Furthermore, the oxidant preparations (M2) contain additional active and auxiliary ingredients. The oxidant preparation (M2) preferably also contains at least one other compound, selected from the group of (i) linear or branched, saturated or unsaturated alcohols with from about 8 to about 20 carbon atoms, (ii) nonionic surfactants, (iii) esters of carboxylic acid with 10 to 20 carbon atoms and linear or branched alcohols with from about 1 to about 5 carbon atoms, (iv) acids and (v) mixtures thereof.

In this context it has been found to be advantageous if the linear or branched, saturated or unsaturated alcohol with from about 8 or about 20 carbon atoms to be selected from the group of myristyl alcohol (1-tetradecanol), stearyl alcohol (1-octadecanol), cetearyl alcohol, 2-octyldodecanol, arachyl alcohol (eicosan-1-ol), gadoleyl alcohol ((9Z)-eicos-9-en-1-ol), arachidon alcohol ((5Z,8Z, 11Z, 14Z)-eicosa-5, 8,11,14-tetraen-1-ol), preferably 2-octyldodecanol and/or cetearyl alcohol, and in a total quantity of from about 0.1 to about 10 wt. %, preferably from about 0.5 to about 5.0 wt. %, particularly from about 1.0 to about 4.0 wt. %, relative to the total weight of the oxidant preparation (M2). The preference is for cetyl alcohol, stearyl alcohol, arachidyl alcohol, behenyl alcohol and lanolin alcohol or mixtures of said alcohols, as available for the large-scale hydration of plant and animal fatty acids, as well as mixtures of said alcohols. The mixture cetearyl alcohol is most preferred.

As contemplated herein, the additional use of at least one nonionic surfactant, particularly an ethoxylated nonionic surfactant is also beneficial. The ethoxylated nonionic surfactant is preferably selected from surfactants with the INCI designation ceteth-12, steareth-12, ceteareth-12, ceteth-20, steareth20, ceteareth-20, ceteth-30, steareth-30, ceteareth-30, oleth-30, ceteareth-50, PEG-40 hydrogenated castor oil and PEG-60 hydrogenated castor oil, as well as mixtures of said substances, most preferably selected from ceteth-20, steareth-20, ceteareth-20, ceteth-30, steareth-30 and ceteareth-30, in a total quantity of from about 0.1 to about 10 wt. %, preferably from about 0.5 to about 5.0 wt. %, more preferably from about 1.0 to about 4.0 wt. %, as well as.

In this connection, it can also be advantageous if the ester from a carboxylic acid with from about 10 to about 20 carbon atoms and a linear or branched alcohol with from 1 to about 5 carbon atoms is selected from isopropylmyristate and contained in a total amount of from about 3.0 to about 25 wt. %, preferably from about 5.0 to about 20 wt. %, particularly from about 8.0 to about 15 wt. % relative to the total weight of the oxidant preparation (M2).

The oxidant preparations (M2) as contemplated herein also contain at least one acid. Preferred acids are selected from dipicolinic acids, food acids, such as citric acid, acetic acid, malic acid, lactic acid and tartaric acid, diluted mineral acids such as hydrochloric acid, phosphoric acid, pyrophosphoric acid and sulfuric acid, as well as mixtures thereof.

The oxidant preparations (M2) preferably have a pH value in the range of from about 2 to about 5, more particularly from about 3 to about 4.

The table below shows most preferred embodiments AF 29 to AF 60 of the oxidant preparations (M2) used as contemplated herein (all values in wt. %, unless otherwise stated):

|  | AF 29 | AF 30 | AF 31 | AF 32 |
|---|---|---|---|---|
| Dimethylcyclosiloxane of formula (I) | 0.1-17 | 0.5-8.5 | 1.0-6.0 | 1.2-4.5 |
| Polydimethylsiloxane of formula (II) | 0.005-3.0 | 0.05-1.5 | 0.1-1.2 | 0.2-1.0 |
| Oxidant | 2.0-20 | 4.0-18 | 3.0-15 | 7.0-12 |
| Cosmetic carrier [1] | Ad 100 | Ad 100 | Ad 100 | Ad 100 |

|  | AF 33 | AF 34 | AF 35 | AF 36 |
|---|---|---|---|---|
| Dimethylcyclosiloxane of formula (I) [2] | 0.1-17 | 0.5-8.5 | 1.0-6.0 | 1.2-4.5 |
| Polydimethylsiloxane of formula (II) [2] | 0.005-3.0 | 0.05-1.5 | 0.1-1.2 | 0.2-1.0 |
| Hydrogen peroxide [3] | 2.0-20 | 4.0-18 | 3.0-15 | 7.0-12 |
| Cosmetic carrier [1] | Ad 100 | Ad 100 | Ad 100 | Ad 100 |

|  | AF 37 | AF 38 | AF 39 | AF 40 |
|---|---|---|---|---|
| Dimethylcyclosiloxane of formula (Ia) | 0.1-17 | 0.5-8.5 | 1.0-6.0 | 1.2-4.5 |
| Polydimethylsiloxane of formula (II) [4] | 0.005-3.0 | 0.05-1.5 | 0.1-1.2 | 0.2-1.0 |
| Hydrogen peroxide [3] | 2.0-20 | 4.0-18 | 3.0-15 | 7.0-12 |
| Cosmetic carrier [1] | Ad 100 | Ad 100 | Ad 100 | Ad 100 |

|  | AF 41 | AF 42 | AF 43 | AF 44 |
|---|---|---|---|---|
| Dimethylcyclosiloxane of formula (Ia) [5] | 0.1-17 | 0.5-8.5 | 1.0-6.0 | 1.2-4.5 |
| Polydimethylsiloxane of formula (II) [5] | 0.005-3.0 | 0.05-1.5 | 0.1-1.2 | 0.2-1.0 |
| Hydrogen peroxide [3] | 2.0-20 | 4.0-18 | 3.0-15 | 7.0-12 |
| Cosmetic carrier [1] | Ad 100 | Ad 100 | Ad 100 | Ad 100 |

|  | AF 45 | AF 46 | AF 47 | AF 48 |
|---|---|---|---|---|
| Dimethylcyclosiloxane of formula (Ia) [5] | 0.1-17 | 0.5-8.5 | 1.0-6.0 | 1.2-4.5 |
| Polydimethylsiloxane of formula (II) [5] | 0.005-3.0 | 0.05-1.5 | 0.1-1.2 | 0.2-1.0 |
| Hydrogen peroxide [3] | 2.0-20 | 4.0-18 | 3.0-15 | 7.0-12 |
| Cetearyl alcohol | 0.1-10 | 0.5-5.0 | 0.8-4.5 | 1.0-4.0 |
| Isopropylmyristate | 3.0-25 | 5.0-20 | 6.0-18 | 8.0-15 |
| Cosmetic carrier [1] | Ad 100 | Ad 100 | Ad 100 | Ad 100 |

|  | AF 49 | AF 50 | AF 51 | AF 52 |
|---|---|---|---|---|
| Hydrogen peroxide [3] | 2.0-20 | 4.0-18 | 3.0-15 | 7.0-12 |
| Cosmetic carrier [1] | Ad 100 | Ad 100 | Ad 100 | Ad 100 |

|  | AF 53 | AF 54 | AF 55 | AF 56 |
|---|---|---|---|---|
| Hydrogen peroxide [3] | 2.0-20 | 4.0-18 | 3.0-15 | 7.0-12 |
| Acid [6] | 0.01-5.0 | 0.05-2.0 | 0.1-1.0 | 0.2-0.8 |
| Cosmetic carrier [1] | Ad 100 | Ad 100 | Ad 100 | Ad 100 |

|  | AF 57 | AF 58 | AF 59 | AF 60 |
|---|---|---|---|---|
| Hydrogen peroxide [3] | 2.0-20 | 4.0-18 | 3.0-15 | 7.0-12 |
| Acid [6] | 0.01-5.0 | 0.05-2.0 | 0.1-1.0 | 0.2-0.8 |
| Linear $C_8$-$C_{20}$ alcohol [7] | 0.1-10 | 0.5-5.0 | 0.8-4.5 | 1.0-4.0 |
| Carboxylic acid ester [8] | 3.0-25 | 5.0-20 | 6.0-18 | 8.0-15 |

| Surfactant [9] | 0.1-10 | 0.5-5.0 | 0.8-4.5 | 1.0-4.0 |
|---|---|---|---|---|
| Cosmetic carrier [1] | Ad 100 | Ad 100 | Ad 100 | Ad 100 |

[1] hydrous cosmetic carrier
[2] weight ratio of dimethylcyclosiloxane of formula (I) to polydimethylsiloxane of formula (II) is from about 6:1 to about 4:1,
[3] quantity specifications relative to 100% hydrogen peroxide
[4] in formula (II), n denotes from about 1,800 to about 28,000,
[5] weight ratio of dimethylcyclosiloxane of formula (I) to polydimethylsiloxane of formula (II) is from about 6:1 to about 4:1, in formula (II) n denotes from about 1,800 to about 28,000,
[6] acid selected from dipicolinic acid, 1-hydroxyethan-1,1-diphosphonic acid, pyrophosphates and mixtures thereof,
[7] linear $C_8$-$C_{20}$ alcohol is selected from 2-octyldodecanol, cetearyl alcohol and mixtures thereof, particularly cetearyl alcohol,
[8] carboxylic acid esters of carboxylic acid with from about 10 to about 20 carbon atoms and a linear or branched alcohol with from 1 to about 5 carbon atoms, particularly isopropylmyristate,
[9] surfactant selected from ethoxylated nonionic surfactants, particularly ceteareth-30 and ethoxylated castor oil In preferred methods for lightening, in step a), one of embodiment forms 1 to 28 of the cosmetic agent (M1) is mixed with one of embodiment forms AF 49 to AF 60 of the oxidant preparation (M2) in the ratio from about 3:1 to about 1:3. Particular preference is given to mixture of one of embodiment forms 21 to 28 of the cosmetic agent (M1) with one of embodiment forms 49 to 60 of the oxidant preparation (M2) in the ratio 1:2.

Use of a lightening agent (AM), which is obtained by mixing one of embodiment forms 1 to 28 of the cosmetic agent (M1) with one of embodiment forms 29 to 60 of the oxidant preparation (M2), achieves improved care and improved lightening effect in a lightening method in comparison with lightening agents which do not contain any siloxanes of formulas (I) or (Ia) and (II).

According to the method, particular preference is given to methods exemplified in that the method results in improved care of the keratinous fibers with a simultaneously improved lightening effect. By using a combination of special siloxanes of formulas (I) or (Ia) and (II), the care and lightening effect resulting from the method are greater than the care and lightening effect which can be achieved when the special siloxanes are absent.

Lightening agents (AM) used as contemplated herein are produced immediately before use from two or multiple separately packaged compositions. This is particularly useful for separating incompatible ingredients in order to prevent a premature reaction. The oxidative lightening agent (AM) is produced by the user immediately before use by mixing the components according to method step a) of the method. As contemplated herein, therefore, the cosmetic agent (M1) is first packaged separately from the oxidant preparation (M2).

Therefore, a further subject of the present disclosure is a package unit (kit-of-parts), comprising—separately packaged— a) at least one container (C1), containing a cosmetic agent (M1), and
b) at least one container (C2), containing an oxidant preparation (M2) which contains at least one oxidant, wherein the cosmetic agent (M1) in container (C1) and/or the oxidant preparation (M2) in container (C2) contains
(i) at least one dimethylcyclosiloxane of the formula (I)

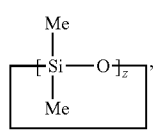

(I)

wherein
z denotes integers from 3 to about 12, and (ii) at least one dimethylcyclosiloxane of the formula (II)

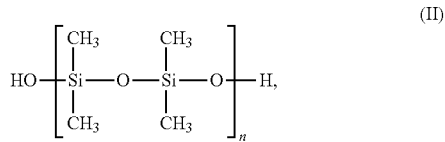

(II)

wherein n denotes integers from about 1,800 to about 28,000

According to the present disclosure, the "container" is an envelope, which is present in the form of a possibly reclosable bottle, tube, jar, bag, sachet or similar envelopes. As contemplated herein, there are no restrictions with respect to the envelope material. However, envelopes from glass or plastic are preferred.

To produce the oxidative dye lightening agents (AM) used in method step a) from the kit-of-parts as contemplated herein, the cosmetic agent (M1) as contemplated herein is mixed in the container (C1) with the oxidant preparation (M2) in container (C2) or vice versa.

Moreover, it can be particularly advantages as contemplated herein for the kit-of-parts to have a further hair treatment agent (M3), more particularly a conditioner preparation, in an additional container. This conditioner preparation contains, advantageously, at least one conditioning agent, selected from the group of cationic polymers, silicone derivatives and oils. Furthermore, the kit-of-parts can comprise application aids, such as combs, brushes, applicators or brushes, personal protective clothing, more particularly disposable gloves, as well as instructions for use. An applicator is a wide brush, located at the stem end of which is a tip, which permits and simplifies the division of fiber bundles and/or hair strands from the total quantity of fibers.

With regard to the dimethylcyclosiloxane of formula (I), the polydimethylsiloxane of formula (II) and the additional active and auxiliary ingredients of cosmetic agent (M1) and oxidant preparation (M2), the statements about the cosmetic agents (M1) and oxidant preparations (M2) used according to the method apply mutatis mutandis.

Finally, a further subject of the present disclosure is the use of a mixture of a combination of
(i) at least one dimethylcyclosiloxane of the formula (I)

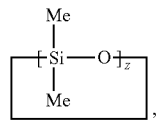

(I)

wherein
z denotes integers from 3 to about 12, and
(ii) at least one polydimethylsiloxane of the formula (II)

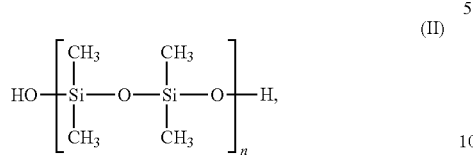

(II)

wherein n denotes integers from about 1,800 to about 28,000 to improve the care of keratinous fibers while simultaneously improving the lightening effect. The term "combination" in the context of the present disclosure is understood to mean a mixture of dimethylcyclosiloxane (i) and polydimethylsiloxane (ii). Use of the aforementioned combinations of special siloxanes results in improved care of dyed keratinous fibers with simultaneous improvement of the lightening effect.

With respect to the preferred embodiments of the use as contemplated herein, the statements made about the cosmetic agents (M1) and oxidant preparations (M2), as well as the kit-of-parts used as contemplated herein apply mutatis mutandis.

The examples below explain, but do not limit preferred embodiments.

EXAMPLES

1. Recipes

Compositions of the used cosmetic agents (M1) (oil-in-water emulsions, all quantities in wt. %). The dimethylcyclosiloxane of formula (I) is preferably a dimethylcyclosiloxane of formula (Ia). The preferably used polydimethylsiloxane has formula (II), where n=from about 1,800 to about 28,000. It is particularly preferable that the weight ratio of dimethylcyclosiloxane of formula (I) and/or (Ia) to polydimethylsiloxane of formula (II) is from about 6:1 to about 4:1.

| Raw material | V1 | E1* |
|---|---|---|
| Xanthan Gum | 0.1 | 0.1 |
| 2-octyldodecanol | 2.3 | 2.3 |
| Lanette N [a] | 14 | 14 |
| Cetearyl alcohol | 3.9 | 3.9 |
| Glycerin monostearate | 6.0 | 6.0 |
| Glycerol 99.5% | 2.0 | 2.0 |
| Coconut amidopropylbetaine, 40% | 2.0 | 2.0 |
| Monoethanolamine | 6.1 | 6.1 |
| 2-Amino-2-methylpropanol | 0.1 | 0.1 |
| Sodium sulfite, anhydrous | 0.1 | 0.1 |
| Caramel syrup, 75% | 0.1 | 0.1 |
| Grapeseed oil | 1.0 | 1.0 |
| p-toluene diamine sulfate | 0.1 | 0.1 |
| Resorcinol | 0.04 | 0.04 |
| m-aminophenol | 0.01 | 0.01 |
| 2,4-diaminophenoxyethanol*2HCl | 0.01 | 0.01 |
| Dimethylcyclosiloxane of formula (I) | — | 1.7 |
| Polydimethylsiloxane of formula (II) | — | 0.3 |
| Water, fully-demineralized | ad 100.00 | ad 100.00 |

*as contemplated herein
[a] INCI designation: Cetearyl alcohol, Sodium cetearyl sulfate (BASF)

The fat basis was fused together at 80° C. and dispersed with a portion of the water quantity. The remaining recipe constituents were then gradually incorporated by agitation. Water was then added to 100 wt. % and the formulation was agitated cold.

Oxidant preparation O1 (all quantities in wt. %)

| Raw material | O1 |
|---|---|
| Di-sodium pyrophosphate | 0.1 |
| Dipicolinic acid | 0.1 |
| Potassium hydroxide 50% | 0.3 |
| 1-hydroxyethan-1,1-diphosphonic acid 60% | 0.4 |
| Sodium fatty alcohol sulfate $C_{16}$-$C_{18}$ | 0.3 |
| Eumulgin RO 40 [b] | 0.6 |
| Cetearyl alcohol | 3.6 |
| Ceteareth-20 | 0.5 |
| Beeswax | 0.3 |
| Isopropylmyristate | 10 |
| Hydrogen peroxide 50% | 23 |
| Water, fully-demineralized | ad 100 |

[b] INCI name: PEG-40 Castor oil (BASF)

2. Improved Nourishment With Use of Special Siloxanes in the Method 12 strands of natural, light-brown European hair (IHIP (New York), lot #03/2012, N121, length 15 cm, weight 1 g) were washed with a hydrous sodium-lauryl ether sulfate solution (3% active substance portion in the solution). The strands were dried in the air and stored for 24 h at 25° C. with 25% relative air humidity. After these strands were softened in water for 5 minutes, their wet compatibility was determined (reference value).

The respective cosmetic agents V1 and E1 were each mixed in a weight ratio 1:2 with the oxidant preparation O1 above to produce the lightening agents (AM-V1) and (AM-E1). The lightening agents (AM-V1) (not as contemplated herein) and (EM-E1) (as contemplated herein) produced above were each applied to 12 strands of natural European hair (IHIP (New York), lot #03/2012, N121, length 15 cm, weight 1 g), wherein 4 g of the respective lightening agent was used per 1 g hair straw. Then the strands were lightened for 30 min at 32° C., rinsed with water for 2 min and dried in the air.

The measurement of wet combability was carried out as follows:

Each of the straws were moistened with water for 2 seconds with a hard rubber comb with fine teeth (Hercules Sagemann, Hamburg Germany). After 3 combing processes were carried out, the combing force was measured during 10 further combing processes, wherein the respective hair straws were slowly rotated during the combing process. The measurements obtained using the statistical tests embedded in the software Statistica 10.0 (StatSoft Inc., USA) were compared:

Shapiro-Wilks Test (test for standard deviation)
Outlier test according to Grubbs
Bartlett Test (test for homoscedasticity of variances)
Univariant significance test
Newman-Keuls Test (determination of significant differences)
Unequal N HSD Test (test for multiple comparisons).

The change of combing force dK in percent can be calculated with the formula $dK=[(K_0-K_i)/K_0]*100$. $K_0$ is the means value of the combing force for the undyed hair straws and $K_i$ is the means value for the hair straws treated with the oxidative lightening agents.

The care of the hair straws increases as the combing force applied to the hair straws decreases and thus the higher the change in combing force is. The dK values for the lightening using lightening agents (AM-V1=not as contemplated herein) and (AM-E1=as contemplated herein) are shown below. The lighting achieved using lightening agents with special siloxanes (AM-E1) demonstrates a greater change of combing force in comparison with the lightening achieved using lightening agents without special siloxanes (AM-V1) and thus improved care.

| Lightening agent | dK [%] |
|---|---|
| AM-V1 (not as contemplated herein) | 33 |
| AM-E1 (as contemplated herein) | 44 |

3. Improved Lightening Effect With Use of Special Siloxanes in the Method

The respective cosmetic agents V1 and E1 were each mixed in a weight ratio 1:2 with the oxidant preparation O1 above to produce the lightening agents (AM-V1) and (AM-E1). The lightening agents (AM-V1) (not as contemplated herein) and (AM-E1) (as contemplated herein) were each applied to strands of dark-blonde, light-brown and dark-brown hair (codes Kerling 6/0, Fischbach & Miller 6923) weighing about 0.7 g, where the weight of the lightening agent applied to the hairs was 4 times the weight of the hairs in each case. Then the strands were lightened for 45 min at 32° C. and rinsed with commercially available shampoo and dried with a hairdryer.

All strands were measured with a colorimeter from Datacolor, type Spectraflash 450. The dL value used for evaluation of the lightening effect is obtained from the L*a*b-color measuring values measured from the respective strands as follows: $dL = L_i - L_0$ $L_0$ is the mean value of the 12 measurements of color measurements for untreated hair strands, whereas $L_i$ is the mean value of the color measurements after lightening of the hair strands with the respective oxidative lightening agents (AM-V1) and (AM-E1).

The higher the dL-value, the higher the lightening effect achieved with the respective lightening agent. The dL values for the lightening using lightening agents (AM-V1) and (AM-E1) are shown below. The lightening achieved using lightening agents with special siloxanes (AM-E1) demonstrates an improved lightening effect in comparison with the lightening achieved using lightening agents without special siloxanes (AM-V1) and thus improved care.

| Lightening agent | dL |
|---|---|
| AM-V1 (not as contemplated herein) | 5.40 |
| AM-E1 (as contemplated herein) | 7.15 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for lightening keratinous fibers, wherein the method comprises the following steps in the specified sequence:

a) applying a lightening agent (AM), which is produced immediately before application, and wherein the lightening agent (AM) is formed by combining a cosmetic agent (M1) and an oxidant preparation (M2), on the keratinous fibers;

b) leaving the lightening agent (AM) produced under step a) on the keratinous fibers for a duration of from about 10 to about 60 minutes, at room temperature;

c) rinsing the keratin fibers with water or a cleansing composition for about 1 to about 5 minutes, wherein the cosmetic agent (M1) comprises;

0.1 to 17% dimethylcyclosiloxane of formula (Ia);

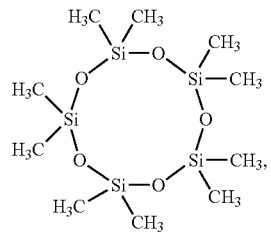

0.005 to 3% by weight of polydimethylsiloxane of formula (II)

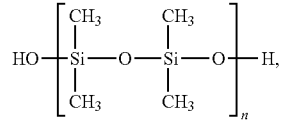

wherein n denotes from about 1,800 to about 28,000;

0.001 to 10% by weight of dyeing compound selected from the group consisting of oxidative dye intermediates, partially-oxidizing dyes and mixtures thereof;

0.0005 to 5% by weight of alkalizing agent;

0.0005 to 5% by weight of thickening agent;

5 to 25% by weight of linear $C_8$-$C_{20}$ alcohol; and cosmetic carriers; and wherein the oxidant preparation (M2) comprises;

0.1 to 17% by weight of dimethylcyclosiloxane of formula (Ia)

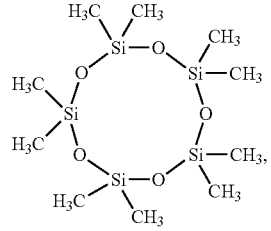

0.005 to 3% by weight of polydimethylsiloxane of formula (II)

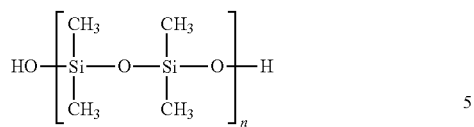
wherein n denotes from about 1,800 to about 28,000;
2-20% weight of hydrogen peroxide; and
cosmetic carrier.
2. The method according to claim 1 wherein, in method step a), the cosmetic agent (M1) is mixed with the oxidant preparation (M2) in the weight ratio from about 3:1 to about 1:3.
* * * * *